United States Patent
Hammer

(10) Patent No.: US 7,276,916 B2
(45) Date of Patent: Oct. 2, 2007

(54) METHOD AND ARRANGEMENT FOR MEASURING CONDUCTIVE COMPONENT CONTENT OF A MULTIPHASE FLUID FLOW AND USES THEREOF

(75) Inventor: Erling Hammer, Mjølkeråen (NO)

(73) Assignee: Epsis AS, Bergen (NO)

( * ) Notice: Subject to any disclaimer, the term of this patent is extended or adjusted under 35 U.S.C. 154(b) by 0 days.

(21) Appl. No.: 10/527,483

(22) PCT Filed: Sep. 10, 2003

(86) PCT No.: PCT/NO03/00313

§ 371 (c)(1),
(2), (4) Date: Nov. 15, 2005

(87) PCT Pub. No.: WO2004/025288

PCT Pub. Date: Mar. 25, 2004

(65) Prior Publication Data

US 2006/0152227 A1    Jul. 13, 2006

(30) Foreign Application Priority Data

Sep. 10, 2002  (NO) .................................. 20024332

(51) Int. Cl.
*G01R 27/04* (2006.01)
*G01R 27/32* (2006.01)
*G01N 37/00* (2006.01)

(52) U.S. Cl. ...................... 324/634; 324/633; 73/61.44

(58) Field of Classification Search ................ 324/634, 324/633; 73/61.44
See application file for complete search history.

(56) References Cited

U.S. PATENT DOCUMENTS

| | | | |
|---|---|---|---|
| 4,458,524 A | 7/1984 | Meador et al. | |
| 4,812,739 A | 3/1989 | Swanson | |
| 5,389,883 A | 2/1995 | Harper | |
| 6,782,736 B1 * | 8/2004 | Hammer | ..................... 73/61.44 |

FOREIGN PATENT DOCUMENTS

| | | |
|---|---|---|
| DE | 196 19 795 | 11/1997 |
| JP | 61204357 A * | 9/1986 |
| WO | 00/52453 | 9/2000 |
| WO | 01/07874 | 2/2001 |
| WO | 02/079770 | 10/2002 |

OTHER PUBLICATIONS

"Development of Electomagnetic Tomography (EMT) for Industrial Applications. Part 1: Sensor Design and Instrumentation" by A.J. Peyton et al; 1st World Congress on Industrial Process Tomography, Buxton, Greater Manchester, Apr. 14-17, 1999.
Patent Abstracts of Japan, vol. 11, No. 203, Jul. 2, 1987 & JP 62025246 A (Kawarada Takashi et al) Feb. 3, 1987.
"Magnetic induction tomography" by H. Griffiths; Measurement Science and Technology.12 (2001).
"Process tomography applied to multi-phase flow measurement" by T. Dyakowski; Meas. Sci. Technol. 7 (1996), pp. 343-353.

* cited by examiner

*Primary Examiner*—Walter Benson
*Assistant Examiner*—Amy He

(57) ABSTRACT

The present invention relates to a method and an arrangement of measuring conductive component content of a multiphase fluid flow and uses thereof. The claimed device comprises two coils arranged around the pipe containing the fluid to be measured, where the induced power loss in the mixture is determined, thereby determining the content of the conductive component. Alternatively, a number of coils are arranged on the outside surface of the fluid transporting pipe and the power loss or attenuation of magnetic field is determined.

14 Claims, 3 Drawing Sheets

METHOD AND ARRANGEMENT FOR MEASURING CONDUCTIVE COMPONENT CONTENT OF A MULTIPHASE FLUID FLOW AND USES THEREOF

CROSS REFERENCE TO RELATED APPLICATION

This application is the U.S. National Stage of International Application PCT/NO2003/000313 filed 10 Sep. 2003 and published in English on Mar. 25, 2004 under International Publication No. WO 2004/025288 claiming priority from Norwegian Patent Application No. 20024332 filed 10 Sep. 2002.

BACKGROUND OF THE INVENTION

1. Technical Field

The present invention relates to a method and arrangement for measuring conductive component content of a multiphase fluid flow. Applications of the method and arrangement are also disclosed.

2. Discussion of Related Art

In particular the method and arrangement are well suitable for determining a water content in flows, in particular in mixtures of oil, HC-gases and water, in a fluid transporting body.

The water fraction meters used in the oil process industry today will all be influenced by the gas content in the oil/water/gas-mixture and different kinds of iterative algorithms are used to compensate for this error. Microwave meters are dependent on the salinity of the water component in both oil and water continuous phases and capacitance meters must be equipped with a conductivity meter to cover the whole range of water fraction from 0 to 100%.

DISCLOSURE OF INVENTION

The object of the present invention is to provide for a method and arrangement to be able to effect determining the content of a conductive fraction in a multiphase flow wherein the conductive phase exist in a range of being continuous or being included in the multiphase flow as droplets.

A multi phase flow of water/oil/gas may exhibit a water-continuous phase or an oil-continuous phase, for example.

In particular the purpose of the invention is to provide for a method and apparatus to determine the conductive water phase in said whole range of water-continuous and oil-continuous phases.

The method according to present invention is characterized by on line measuring the fraction of the conductive component in the multi phase flow by using a coil design optimized for non-conductive continuous mixtures, and a coil optimized for conductive continuous mixtures.

The preferred embodiments appear as described below in detail.

The arrangement according to present invention is for determining water content in multi phase flows in a fluid transporting body comprising a coil design optimized for non-conductive continuous mixtures, and a coil optimized for conductive continuous mixtures. Preferred embodiments of the arrangement appear in detail below.

According to the invention, the above-mentioned method and arrangement, are suitable for determining the water content of a multi phase flow of oil, hydrocarbon gases and water, in that water is the conductive component to be determined, and the oil and gas phases being the non-conductive phase.

According to a specific embodiment, the method is used for measuring the water content in oil/gas/water multiphase mixture flows wherein the different phases in the crude are separated, i.e. not homogeneously mixed.

In the following, the invention will be disclosed in relation to a multi phase mixture of water, oil and gas, while it should be evident that it may be applied to any multi phase mixture including one liquid conductive phase.

The water fraction meter described thus can detect the water fraction in three phase flows on line independent of the gas content in the mixture. Today the conductivity of the water component is determined off line by laboratory tests of processed water. The described instrument can monitor the water conductivity on line.

BRIEF DESCRIPTION OF THE INVENTION

The invention will be explained more in detail by referring to the enclosed drawing figures, in which.

Figure 3:
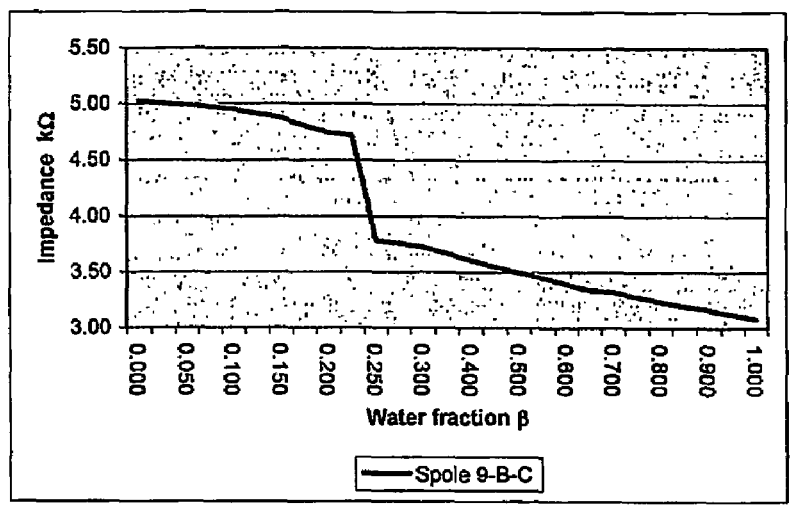

FIG. 3 shows the result of an experiment measuring an oil/gas/water mixture phase with a particular coil design, with the impedance shown as a function of the water fraction in a multi phase flow to be determined. This coil design is sensitive for the water content in the mixture over the whole range, i.e. from the oil continuous phase to the water continuous phase. The steep area of the curve represents the transition area between the oil-continuous (left side of curve) and water-continuous phases (right side of curve).

Figure 4:
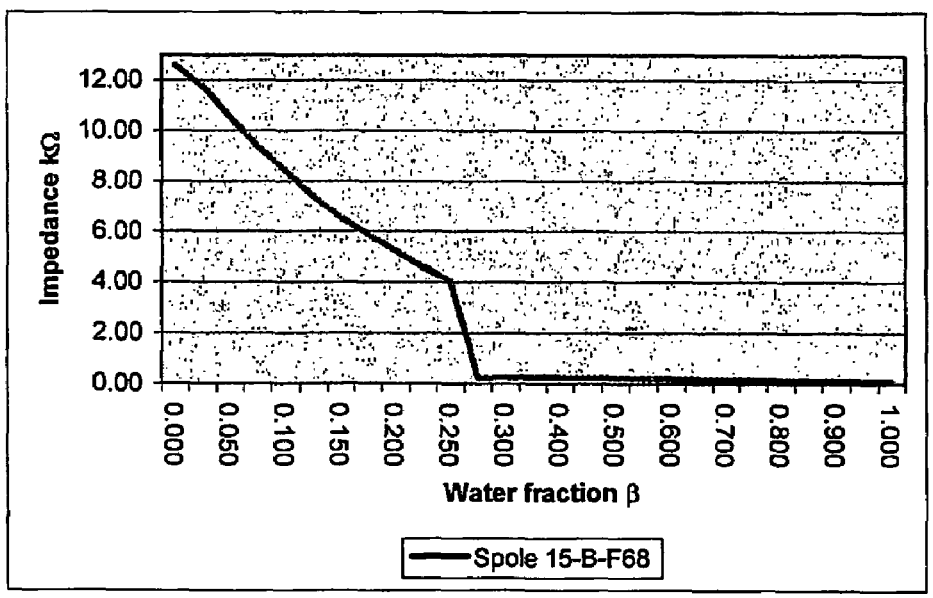

FIG. 4 shows the results of measurements effected with a coil which has increased sensitivity for oil/gas continuous mixtures (the left side of curve).

Figure 5:
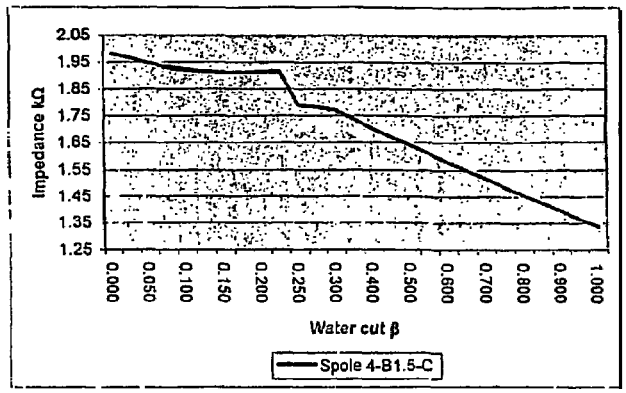

FIG. 5 shows the measurement results of using a coil configuration of an increased sensitivity for water continuous mixtures (right hand side of curve).

Figure 6:
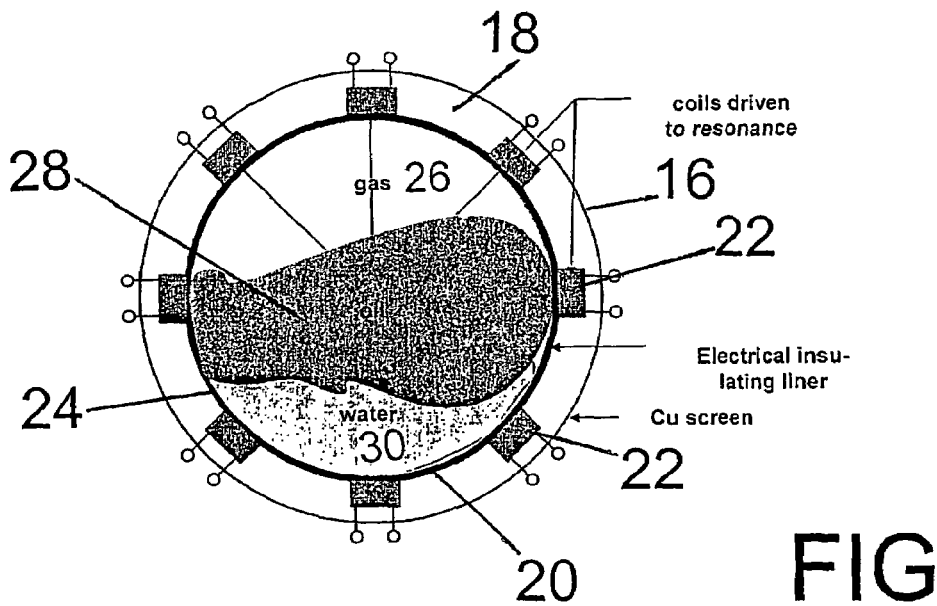

FIG. 6 shows an arrangement for utilizing this induction principle in a tomographic arrangement.

Figure 7:
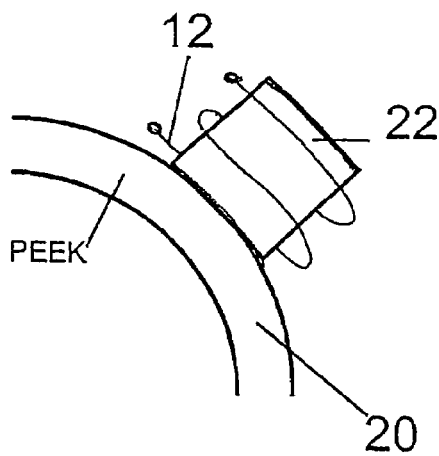

FIG. 7 shows a detail of a coil unit design which is connected to the pipe surface.

BEST MODE FOR CARRYING OUT THE INVENTION

Measurement Principle

Figure 1:
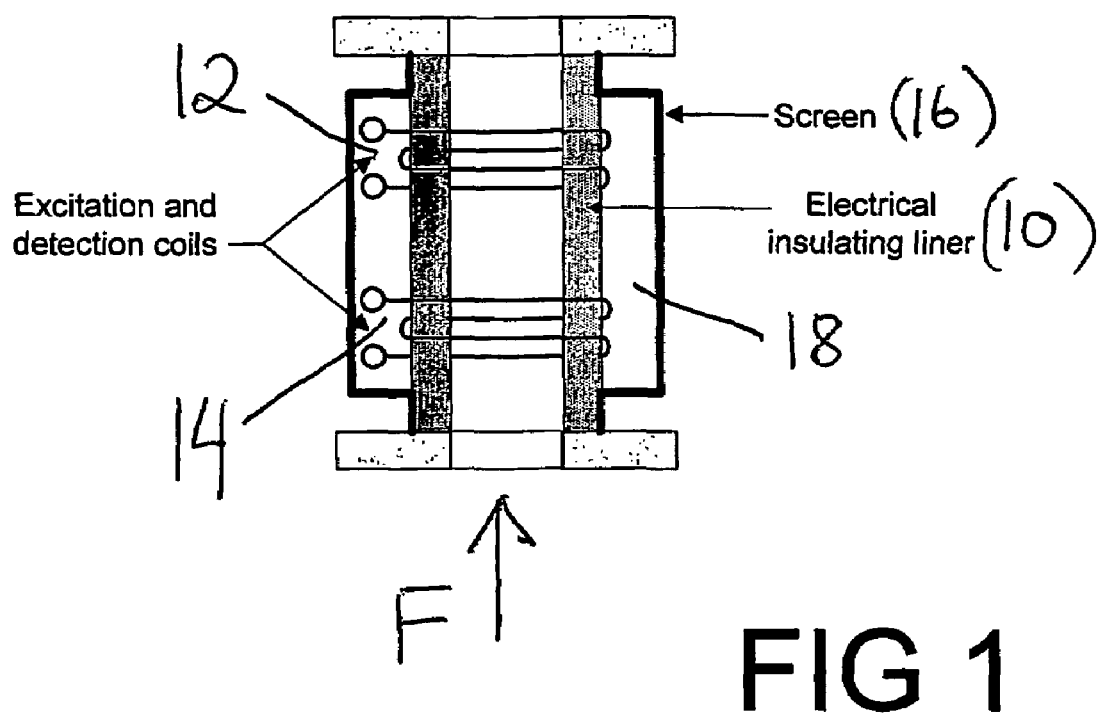
FIG. 1 shows a section of the arrangement/instrument (the meter spool principle) according to the invention.

A sketch of the meter spool pipe principle is shown in the enclosed FIG. 1. There is shown an electrical insulated liner 10 (a coil pipe) around which excitation and detection coils 12,14 are arranged. The insulated liner may be a pipe prepared of a ceramic, plastic or a peek material and is, with all elements installed, arranged to be inserted in fluid flow conducting pipe. The coils 12,14 are protected by a screen (a steel material) 16 enclosing the central pipe section. The space between the screen and the pipe outer surface is filled with an inert material. The purpose of the screen to make resistance to the fluid flow pressure inside the liner 10. Each coil having reference numbers 12 and 14 is used as an excitation coil and a detection coil. The coils are parts of an oscillator unit supplying alternating voltage to the coils. The oscillator frequency is dependent on the inductance and capacitance of each coil. Each coil 12 and 14 includes a different number of coil windings. The coil wires are preferably made of flat Cu-lices (copper), of a rectangular cross section, the thickness of which being up to 40 um in order to avoid any influence of changing resistance as the frequency is changing. This appears in FIG. 1. The direction of the multi phase flow through the pipe is shown by F.

Each coil (12 or 14 in FIG. 1) can be regarded as a parallel coupling between an inductance, a capacitance and a resistance. The capacitance consists of different spread capacitances between the coil windings and an equivalent parallel resistance made up by the resistance in the coil windings and the power loss in the volume of the mixture flowing through the coil. The first one is constant but the second one is dependent on the amount of water in the mixture. The coil is part of a feedback circuit which latches the excitation frequency to the coil's resonant frequency. The current in the feedback loop will then be dependent on the induced power loss in the mixture. The resonant frequency can be determined by the number of windings in the coil and the optimal frequency range will be dependent on the current penetration depth and the induced power loss in the multi phase flow mixture. The higher the frequency the higher is the loss and thus the higher is the sensitivity of the meter, but the frequency is limited by the current penetration depth of the induced current in both the mixture and the coil windings.

In oil/gas continuous mixtures the water consists as insulated droplets in the oil/gas. The induced loss in these distributed droplets is small compared to the loss in water continuous mixtures (this is the reason for making the power transformer cores of thin insulated steel plates). However, the penetration depth of the eddy currents is large so we can use a higher resonance frequency and thus increase the sensitivity.

Due to this fact two coils are used in the meter according to the invention, and they are simultaneously optimized for oil/gas continuous mixtures and water continuous mixtures respectively.

The induced loss will be dependent on the conductivity in the water component. By using two different coils with different resonance frequencies it is possible to compensate for variation in the conductivity and hence the conductivity of the water can be determined as well.

To keep the coil resistance constant it is important to avoid the frequency dependent resistance in the coil windings due to the electrical penetration depth. This can be avoided by winding the coil with a cable of separately insulated Cu-lices with a radius less than the electrical skin depth of Cu. In our experiment we have used flat Cucords at a thickness of 40 um.

Theory

The eddy current loss in an infinitely large plate with thickness d (meter) and electrical conductivity a ohm-meter$^{-1}$, penetrated by a magnetic field B (Tesla) parallel the plate at a frequency w (radians/second), is:

$$P_0 = \frac{\sigma \omega^2 d^2 B^2}{12} \quad (1)$$

where B is the rms-value of the penetrating magnetic field, a the conductivity of the medium and co the frequency of the magnetic field. The resonance frequency for the different coils lays in the region of 2 to 8 MHz and the electrical conductivity in processed water from the North Sea oil is 4-6 (ohm-meter)$^{-1}$.

The skin depth for the electrical current induced in a conducting medium is:

$$\delta = \sqrt{\frac{2}{\mu_0 \mu_r \omega \sigma}} \quad (2)$$

where $\mu_o$ and $\mu_r$ are the magnetic permeability for the empty space and the relative permeability respectively.

At a frequency of 5.5 MHz which is used for the most sensitive coil for water continuous mixtures the penetration depth for the eddy currents will approximately be 10 cm. This is acceptable for production pipes up to a diameter of 20 cm (8"). The frequency may preferably be in the range of 1-10 MHz, and most preferably in the range of 2 to 8 MHz.

Figure 2:
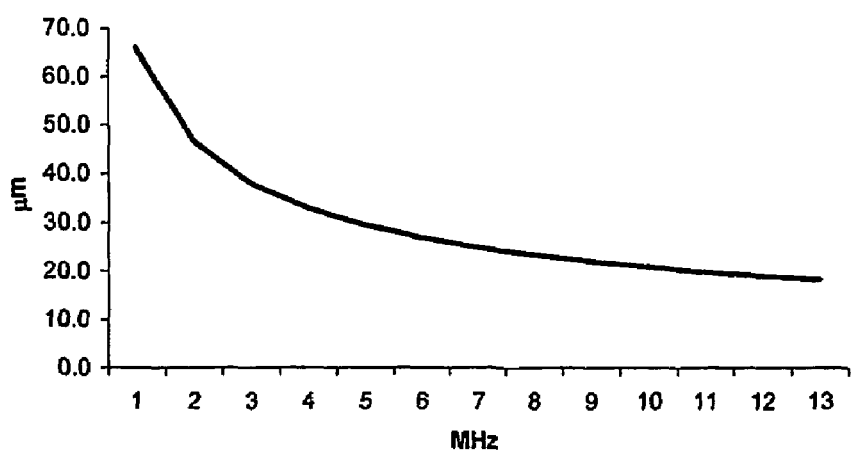
FIG. 2 shows a curve of the penetration depth as a function of the frequency of the coil, i.e. the skin depth in micrometers of the Cu lead (conductor) of the coil as a function of frequency (Mhz).

The skin depth in micrometers of the Cu lead in the coil as a function of frequency (Mhz) is shown in the following FIG. 2. The figure shows that the thickness of the Cu lead preferably is up to 40 μm.

The coil design of the instruments used in the experiments are as follows:

FIG. 3. Nine layer 9 windings of flat Cu-cord (15×0.04 mm). f=5.5 MHZ

FIG. 4. One layer, 15 windings of flat Cu-cord, f=2 MHz

FIG. 5. 4 layers, 4 winding coil of flat Cu-cord. f=9 kHz.

Experimental Results

FIG. 3 shows the meter result from a 9-turn coil which is sensitive for the water content in the mixture over the whole range. The impedance kΩ is shown as a function of the water fractionβ. The diagram shows that with this meter coil structure the whole range may be determined by the use of one coil only. A change in water content will effect a determinable (or visible) change in the impedance over the whole range.

FIG. 4 shows a coil which has an increased sensitivity for oil/gas continuous mixtures. Thus, in the oil/gas continuos range, there is marked reduction in impedance as the water fraction increases and a change of water content in the fluid mixture is possible to measure in this range. But it is almost impossible to measure a change in water fraction exceeding about 0.275, as the impedance remains constant within said range.

FIG. 5 gives the result from the application of a coil configuration that has an increased sensitivity for water continuous mixtures. Thus, in the water continuous range, there is a marked reduction in impedance as the water fraction increases, and therefore a change of water content in the fluid mixture is possible to measure in this range. But it is almost impossible to measure a change in water fraction up to about 0.2 as the impedance does not change much within this range.

By combining those two last coils used in example 4 and 5, in a meter according to the invention, an increased sensitivity can be obtained both in water discontinuous mixtures and water continuous mixtures.

the Principle Used in Process Tomography

When the different phases in the crude are separated, i.e. not homogeneously mixed, the water content can not be measured with the same accuracy as for homogeneous mixtures if the principle explained above is used.

The arrangement for utilizing this induction principle in a tomographic arrangement is shown in FIG. 6.

FIG. 6 is a proposed coil arrangement which coils together form a meter for tomographic detection of multiphase flow. The figure shows a pipe section 20 of the same material as illustrated in FIG. 1. To the outside surface of the pipe 20, a number of 8 coil units 22 are mounted in close contact with the pipe surface 24. The three phases of gas 26, oil 28 and water 30 are shown inside the pipe section. The water amount may now be measured by means of the arrangement according to FIG. 6.

A more detailed drawing of one of the coils 22 is shown in FIG. 7.

Here we can determine the power loss generated in the alternating magnetic field from one coil at a time. Based on mathematical models of the magnetic field from the coils it is possible to work out a reconstruction algorithm for imaging the water distribution in the meter cross section. It may also be possible to excite one of the coils at a time and use all the other coils as pick up coils and detect the attenuation of the magnetic field from the transmitter to the receiver coils and thus reconstruct a picture of the area of low field penetration which must be areas of water.

In the new solution, a different electronics is used. Here a resonance circuit is used wherein the resonance frequency changes as a function of changes in water content and salinity. Also the impedance at resonance changes due to these changes. By using a resonance circuit the frequency is always locked at the resonance frequency, wherein the sensitivity for changes is greatest. Thus one saves one coil so that the new solution is cheaper and simpler.

In an oil-water mixture the flow may be divided in oil-continuos flows at low water fractions and water-continuos flows at low oil fractions. As can be seen from the plot, where the impedance is plotted as a function of the water fraction, the curve exhibits a discontinuity. At this point, the flow changes from oil-continuos to water-continuos or vice versa. See FIGS. 3,4 and 5.

Measurements have shown that the sensitivity in the two areas depends on the number of windings and whether the coil is wound with standard copper wire or copper tape.

This provides for excellent flexibility where the sensitivity may be optimized for a given application, for example if one wishes to obtain a maximum sensitivity for low water fractions in oil. In another application one may wish a maximum sensitivity for low oil fractions in water. This requires two different coils according to the invention, and if two coils according to FIG. 1 are combined, a maximum sensitivity over the whole of the measuring area (see FIGS. 4 and 5) is obtained. A possibility to compensate for changes in salinity is another advantage which may be obtained.

REFERENCES

[1] Maxwell, J. C.: "A Treatise on Electricity & Magnetism" The Clarendon Press, Oxford, Vol. 1, 1st edition 1873.
[2] Bruggeman, D. A. G.: "Berechnung verschiedener physikalischer Konstanten von heterogenen Substanzen". Annalen der Physik, 5. Folge, Band 24, 1935
[3] Ragnvald Soldal, Detection of Water Cut and Levels in Separator Using High Frequency Magnetic Field (In Norwegian), Cand. Scient Thesis, University of Bergen, 1999.
[5] A J Peyton, M S Beck, A R Borges, J E de Oliveira, G M Lyon, Z Z Yu, M W Brown, J Ferrerra, Development of Electromagnetic Tomography (EMT) for Industrial Applications. Part 1: Sensor Design and Instrumentation. Proceedings of 1st World Congress on Industrial Process Tomography, Buxton, Greater Manchester, Apr. 14-17, 1999, 306. Data supplied from the esp@cenet database

The invention claimed is:

1. A method, comprising:
   performing an on-line measurement of a water fraction in a multi-phase flow of a multi-phase mixture in a pipe by measuring at resonance impedances of coils disposed about said pipe, said impedances varying as a function of a composition of conducting fractions present in the flow, and by employing said coils comprising:
   a first coil including a first number of turns, said first coil optimized for measuring a continuous mixture of oil/gas, and
   a second coil including a second different number of turns, said second coil optimized for measuring a continuous mixture of water, wherein
   said coils are disposed in operation on an outer surface of said pipe, such that the coils are arranged so as to be driven at resonant frequencies of said coils in operation,
   wherein losses arising in the coils at resonance are determined by alternating from one of the coils to another thereof.

2. The method as claimed in claim 1, comprising employing a computer simulation algorithm for generating a view of the water fraction over a cross-section of the pipe based upon a mathematical model of magnetic fields generated by the coils.

3. A method as claimed in claim 1, comprising at any given moment of time, operating one of the plurality of coils to function as a transmitting coil to generate a magnetic field, and employing the other coil as a detector coil for detecting a reduction of the magnetic field and generating a view of a region of the pipe whereat the magnetic field is low and thereby indicative of a region including water.

4. The method as claimed in claim 1, comprising operating two of the coils at mutually different frequencies for compensating for variations due to water content and thereby determining the water content.

5. The method as claimed in claim 1, wherein at least one coil winding is implemented using cable comprising individually insulated wires or conductors.

6. The method as claimed in claim 1, wherein at least one coil winding is implemented using copper strips which are formed into a thickness which is less than a skin-depth effect of the magnetic fields into the flow through the pipe.

7. The method as claimed in claim 1, wherein at least one of the coils is implemented using flat copper conductor strips having a thickness of 40 µm.

8. The method as claimed in claim 1, wherein the coils are arranged in operation to operate at resonant frequencies in a range of 2 to 8 MHz.

9. The method as claimed in claim 1, comprising employing a resonance frequency of 5.5 MHz for the coils in order to achieve a magnetic field penetration depth of substantially 10 cm into the flow.

10. The method as claimed in claim 1, comprising employing a multi-turn coil for at least one of said coils which is sensitive to water content over a whole region of the pipe.

11. A device, comprising:
    a first coil with a number of windings, said first coil optimized for measuring in operation a mixture of oil/gas flowing through a pipe; and a second coil with a different number of windings, said second coil optimized for measuring in operation a continuous mixture of water flowing through the pipe, such that the device is operable to provide an on-line measurement of a water fraction in the multi-phase flow by measuring coil impedances at resonance, said impedances varying in response to a proportion of conducting fraction present in the flow through the pipe, wherein said first coil and said second coil are arranged on an outside surface of the flow-conducting pipe for operating at resonance.

12. The device as claimed in claim 11, wherein loss of power at resonance associated with an alternating magnetic field is measured for one coil at a time.

13. The device as claimed in claim 11, wherein a simulation algorithm is employed for generating a view of a water distribution flowing in a cross-section of the pipe, said simulation based upon a mathematical model of magnetic fields generated by the coils in operation.

14. The device as claimed in claim 11, wherein, during operation of the device, one at a time of the first coil and the second coil is arranged for functioning as a transmitting coil for generating a magnetic field penetrating into the flow through the pipe, and at least one other coil of said first coil and said second coil is employed as at least one receiving coil for use in detecting a reduction in the magnetic field coupled in operation from the at least one transmitting coil to the at least one receiving coil and thereby reconstructing a view of a region of the pipe having reduced magnetic field penetration, said region corresponding to regions including water.

* * * * *

UNITED STATES PATENT AND TRADEMARK OFFICE
CERTIFICATE OF CORRECTION

PATENT NO. : 7,276,916 B2  Page 1 of 1
APPLICATION NO. : 10/527483
DATED : October 2, 2007
INVENTOR(S) : Erling Hammer It is certified that error appears in the above-identified patent and that said Letters Patent is hereby corrected as shown below:

In column 3, line 56 "a" should be --σ--.

In column 4, line 63 "the" should be --The--.

Signed and Sealed this

Thirty-first Day of March, 2009

JOHN DOLL
*Acting Director of the United States Patent and Trademark Office*